United States Patent [19]

Bluestein et al.

[11] 4,209,373

[45] Jun. 24, 1980

[54] ACIDIC AGAR GEL ELECTROCHROMATOGRAPHY OF HEMOGLOBINS

[75] Inventors: Barry I. Bluestein, Lansing; Cyrus A. Lepp, Corning; Robert D. Mason, Painted Post, all of N.Y.

[73] Assignee: Corning Glass Works, Corning, N.Y.

[21] Appl. No.: 44,471

[22] Filed: Jun. 1, 1979

[51] Int. Cl.$^2$ .................... G01N 33/16; G01N 27/26
[52] U.S. Cl. .................... 204/180 G; 23/230 B; 424/12
[58] Field of Search .................... 204/180 G, 299 R; 424/12; 23/230 B

[56] References Cited

U.S. PATENT DOCUMENTS

| | | | |
|---|---|---|---|
| Re. 24,752 | 12/1959 | Ressler | 204/180 G |
| 3,497,437 | 2/1970 | Louderback et al. | 204/180 G |
| 3,558,459 | 1/1971 | Granstrand et al. | 204/180 G |
| 3,607,695 | 9/1971 | Schneider | 204/180 G X |
| 3,692,654 | 9/1972 | Svendsen | 204/180 G X |

*Primary Examiner*—Arthur C. Prescott
*Attorney, Agent, or Firm*—William E. Maycock; Clinton S. Janes, Jr.

[57] ABSTRACT

The common hemoglobin variants A, $A_2$, F, S, and C are discretely separated by electrochromatography under acidic conditions on an agar gel which utilizes an agar gel having a wet thickness of from about 0.1 to about 0.5 mm. and a potential of from about 60 to about 110 volts. The gel buffer is a citrate buffer having a citrate concentration of from about 0.04 to about 0.065 M and a pH of from about 6.0 to about 6.5. The well buffer is a citrate buffer having a citrate concentration of from about 0.055 to about 0.065 M and a pH of from about 6.0 to about 6.5.

23 Claims, No Drawings

4,209,373

ACIDIC AGAR GEL ELECTROCHROMATOGRAPHY OF HEMOGLOBINS

BACKGROUND OF THE INVENTION

Interest in population-screening programs for abnormal hemoglobins in the United States has increased primarily because of the National Sickle Cell Disease Program developed by the Department of Health, Education and Welfare. Thus, screening for hemoglobinopathies has become very important within the past five years. For example, many hospitals now screen all incoming surgical patients for such abnormalities. Because electrophoresis on cellulose acetate is the primary procedure used in the Federal Sickle Cell Disease Program, cellulose acetate electrophoresis at pH 8.4–9.2 currently is the most common electrophoretic screening method for hemoglobinopathies. It has been found, however, that cellulose acetate cannot adequately separate certain combinations of hemoglobin variants. See, for example, E. J. Hicks and D. J. Hughes, Clin. Chem., 21, 1072 (1975). Thus, in questionable cases, one must proceed to a secondary procedure such as electrophoresis (electrochromatography) on citrate agar to obtain a more definitive diagnosis.

The use of citrate agar in the electrophoresis of hemoglobin variants has been summarized by R. J. Wieme, "Agar Gel Electrophoresis", Elsevier Publishing Company, Amsterdam, 1965. The typical citrate agar procedure involves the use of a gel buffer having a citrate concentration of 0.05 and a pH of 6.2, with only minor variations, if any, in pH or citrate concentration. See, for example, C. N. LeCrone et al., Clin. Chem., 22, 1743 (1976).

The hemoglobin variants separated by the citrate agar electrochromatography procedure can be estimated visually, scanned by a densitometer to determine the relative amounts of each variant present, or stained to enhance visualization or densitometry readings of the hemoglobin variants. Typical staining procedures, however, involve hemoglobin-specific dyes such as benzidine or o-dianisidine. Benzidine is a known carcinogen and has been removed from the market by the Federal Food and Drug Administration. The o-dianisidine is a benzidine derivative and is suspected to be carcinogenic as well; thus, such compound also may be removed from the market. In addition, these stains are light sensitive and darken upon storage. Furthermore, the prior art agar gels must be stored wet and thus can be bulky and difficult to store.

SUMMARY OF THE INVENTION

Accordingly, the present invention provides, in a method for discretely separating the common hemoglobin variants A, $A_2$, F, S, and C by electrochromatography on an agar gel, under acidic conditions utilizing citrate gel and well buffers, each of which has a citrate concentration of approximately 0.05 M and a pH of approximately 6.0, and a potential of 50–90 volts, the improvement which comprises employing:

A. an agar gel having a wet thickness of from about 0.1 to about 0.5 mm. and

B. a potential of from about 60 to about 110 volts.

In a preferred embodiment, the separated hemoglobin variants are visualized by means of a nonspecific protein stain, such as amido black. Such stain is used in place of the prior art hemoglobin-specific stains, which stain is nontoxic, not sensitive to light, and highly sensitive to the protein content of the hemoglobin variants.

DETAILED DESCRIPTION OF THE INVENTION

The theoretical basis of the separation described and claimed herein can be characterized as electrochromatography, which term perhaps is more appropriate than the term "electrophoresis" because of (1) the migration and separation of the hemoglobins being achieved largely by the combination of interactions between the proteins in question and fixed, charged molecules in the agar gel, (2) the electroendoosmotic flow in the gel, and (3) the field strength applied. While the term "electrophoresis" is used almost exclusively in the prior art, it is clear that the principles of electrochromatography were recognized some time ago; see, for example, Wieme, supra at pp. 192–195. Accordingly, the term "electrochromatography" is used throughout this disclosure to refer to electrophoresis-type separations of proteins on agar gel under acidic conditions.

The method of the present invention requires the use of an agar gel having a wet thickness of from about 0.1 to about 0.5 mm. The nature of the agar is not critical. Suitable agar preparations are readily available commercially and have been found to be suitable in the method of the present invention. The amount of agar typically employed is about 1% weight per volume. It will be apparent to those having ordinary skill in the art that greater or lesser amounts of agar can be employed, provided that appropriate adjustments in the other parameters are made.

Optionally, the gel can contain minor amounts, e.g. less than about 10% weight per volume, of one or more humectants. Examples of suitable humectants include sucrose, hydroxyethylcellulose, glycerin, sorbitol, and the like. A particularly useful amount of humectant is 5%, with sucrose being the preferred material. The humectant aids in the retention of small amounts of water at the surface, thereby stabilizing the wet film. The humectant also serves as a dried film stabilizing agent. The use of a humectant such as sucrose is preferred.

In addition, the gel also can contain a small amount of a wetting agent which acts as a dried film stabilizing agent. The use of the wetting agent is, in practice, preferred. Typically, the wetting agent will be present in an amount less than about 0.1% weight per volume. The suitable wetting agents include anionic and nonionic surfactants, as well as other compounds having properties of a wetting agent. Examples of such compounds include, among others, polyvinyl alcohol, sulfate esters of alkyl phenoxy polyoxyalkylene alkanols, alkyl aryl sulfonates, alkali metal salts of the sulfates and sulfonates, fatty acid soaps, polyether alcohols, and the like. In addition to polyvinyl alcohol, specific examples of such wetting agents include, among others, nonyl phenyl polyoxyethylene sulfate, sodium lauryl sulfate, and nonyl phenyl polyoxyethylene ethanol. The preferred wetting agent is polyvinyl alcohol, provided that such material is essentially free of polyvinyl acetate.

Finally, it should be noted that the gel can contain up to about 1% weight per volume of agarose. Such use of agarose, however, is optional. If used, a preferred amount of agarose is 0.5% weight per volume. In addition, the gel can contain small amounts of preservatives, such as sodium azide and disodium ethylenediaminetetraacetate.

The citrate gel buffer is prepared from sodium citrate and citric acid in accordance with well known procedures. The concentration of citrate in the buffer can range from about 0.04 to about 0.065 M. A particularly useful concentration is 0.055 M, in which case the buffer is readily prepared by dissolving 16.17 g. of sodium citrate dihydrate in 990 ml. of deionized distilled water, after which the pH is adjusted as desired with 30% weight per volume citric acid solution. The gel buffer pH typically can vary from about 6.0 to about 6.5, with a pH of about 6 being preferred. In the example just given, the concentration of sodium citrate is 0.055 M, while the total citrate concentration, which includes both citrate and citric acid, is about 0.06 M.

As already pointed out, the gel must have a thickness of from about 0.1 to about 0.5 mm. A particularly preferred wet thickness is from about 0.3 to about 0.4 mm. While the gel can be prepared by any known method, a most convenient means of gel preparation is the use of cassette-type molds, such as are disclosed in U.S. Pat. Nos. 3,499,265 and 3,635,808.

The citrate well buffer similarly is prepared in accordance with known procedures. In general, the citrate concentration will be in the range of from about 0.055 to about 0.065 M, with a concentration of about 0.06 M being preferred. The pH of the well buffer can vary from about 6.0 to about 6.5, with a pH of 6.0 being preferred.

The electrophoresis is carried out in accordance with well known procedures, using a potential of from about 60 to about 110 volts. The preferred potential is about 90 volts.

If desired, the amounts of hemoglobin variants thus separated can be estimated by visually inspecting the gel. Such amounts can be quantitated, however, by various known methods. For example, the gel can be scanned directly in a densitometer, taking advantage of the heme color in the variants. Alternatively, the variants can be visualized indirectly by staining them with a nonspecific protein stain such as amido black or Ponceau S, followed by scanning in a densitometer at an appropriate wavelength. Other methods, of course, will be readily apparent to those having ordinary skill in the art.

The method of the present invention is further illustrated, but not limited, by the example which follows. Unless otherwise specified, all temperatures are in degree Celsius.

Materials and Methods

Gel Buffer

The gel buffer, which was 0.055 M in sodium citrate, was prepared by dissolving 16.17 g. of sodium citrate dihydrate in 990 ml. of deionized distilled water. The pH was adjusted to 6.0 with 30% weight per volume citric acid solution.

Gel Composition

The gel solution was prepared by combining 1.0 g. of Bacto-agar (Difco), 0.5 g. agarose, 5 g. sucrose, 20 mg. polyvinyl alcohol, and 30 mg. of disodium ethylenediaminetetraacetate with 100 ml. of gel buffer. The resulting mixture was heated, with stirring, in a boiling water bath for 30 minutes after total dissolution of the components had occurred.

Preparation of Gel Films

Empty cassette molds were obtained from Corning Medical (Corning Glass Works, Medfield, Massachusetts) and used to form the thin gels. The gel solution was cooled to 65°–70° before being injected into the nipple of the mold with a glass syringe to which a piece of plastic tubing, 3 mm. in diameter, was attached. The mold was held in an upright position during injection to facilitate removal of air from the upper nipple. After injecting about 5 ml. of gel solution, the cassette mold was placed on a flat benchtop, and a flat weight of about 500 g. was placed on the mold to expel any excess gel. After the gel solution had set (about 5 minutes at ambient temperature), each gel was wrapped in stretch plastic and aluminum foil and stored at 4° for 24 hours before use. The gels thus prepared were stable for at least 6 months if kept tightly sealed.

Well Buffer

The buffer, which was 0.0635 M, was prepared by mixing 16.9 g. of sodium citrate dihydrate and 1.23 g. of anhydrous citric acid and adding sufficient deionized distilled water to make one liter of buffer. The resulting buffer had a pH at room temperature of 6.0.

Electrophoresis

Hemoglobin samples from lysed red blood cells were applied in 1 μl. aliquots to the indented sample wells of the gel films. 80 ml. of cold (4°) well buffer was added to each well of a Corning-ACI electrophoresis apparatus. The gel plate (on a thin polystyrene backing) was placed in the gel holder-cover and placed on the cell base with the origin towards the anode. A constant voltage of 90 volts was applied across the plate for 35 minutes at room temperature. The plate then was removed and placed in a staining solution consisting of 0.2% weight per volume amido black 10B in 5% acetic acid. The staining time was 3 to 5 minutes, after which the plate was rinsed briefly in 5% acetic acid and dried. The plate then was completely destained in the dilute acetic solution.

The method described herein resulted in the discrete and complete separation of all samples into the appropriate bands, thereby completely separating hemoglobins A, $A_2$, F, S, and C.

What is claimed is:

1. In a method for discretely separating the common hemoglobin variants A, $A_2$, F, S, and C by electrochromatography on an agar gel, under acidic conditions utilizing citrate gel and well buffers, each of which has a citrate concentration of approximately 0.05 M and a pH of approximately 6.0, and a potential of 50–90 volts, the improvement which comprises employing:
   A. an agar gel having a wet thickness of from about 0.1 to about 0.5 mm. and
   B. a potential of from about 60 to about 110 volts.

2. The method of claim 1 in which the gel wet thickness is from about 0.3 to about 0.4 mm.

3. The method of claim 1 in which the potential is about 90 volts.

4. The method of claim 1 in which the gel contains a humectant at a level of from about 0 to about 10% weight per volume.

5. The method of claim 4 in which the humectant is sucrose.

6. The method of claim 5 in which the sucrose is present at a level of about 5%, weight per volume.

7. The method of claim 1 in which the gel contains a wetting agent at a level of from about 0 to about 0.1%, weight per volume.

8. The method of claim 7 in which the wetting agent is polyvinyl alcohol.

9. The method of claim 8 in which the polyvinyl alcohol is present at a level of about 0.02%, weight per volume.

10. The method of claim 1 in which the gel contains agarose at a level of from 0 to about 10%, weight per volume.

11. The method of claim 10 in which the agarose is present at a level of about 0.5%, weight per volume.

12. In a method for discretely separating the common hemoglobin variants A, $A_2$, F, S, and C by electrochromatography on an agar gel, under acidic conditions utilizing citrate gel and well buffers, each of which has a citrate concentration of approximately 0.05 M and a pH of approximately 6.0, a potential of 50–90 volts, and a hemoglobin-specific stain to visualize the separated hemoglobin variants, the improvement which comprises employing:
   A. an agar gel having a wet thickness of from about 0.1 to about 0.5 mm.,
   B. a potential of from about 60 to about 110 volts, and
   C. a nonspecific protein stain to visualize the separated hemoglobins.

13. The method of claim 12 in which the gel wet thickness is from about 0.3 to about 0.4 mm.

14. The method of claim 12 in which the potential is about 90 volts.

15. The method of claim 12 in which the nonspecific protein stain is amido black.

16. The method of claim 12 in which the gel contains a humectant at a level of from about 0 to about 10%, weight per volume.

17. The method of claim 16 in which the humectant is sucrose.

18. The method of claim 17 in which the sucrose is present at a level of about 5%, weight per volume.

19. The method of claim 12 in which the gel contains a wetting agent at a level of from about 0 to about 0.1%, weight per volume.

20. The method of claim 19 in which the wetting agent is polyvinyl alcohol.

21. The method of claim 20 in which the polyvinyl alcohol is present at a level of about 0.02%, weight per volume.

22. The method of claim 12 in which the gel contains agarose at a level of from 0 to about 1%, weight per volume.

23. The method of claim 22 in which the agarose is present at a level of about 0.5%, weight per volume.

* * * * *